United States Patent [19]
Kraus et al.

[11] Patent Number: 5,246,420
[45] Date of Patent: Sep. 21, 1993

[54] HIGHLY STEERABLE DILATATION BALLOON CATHETER SYSTEM

[75] Inventors: Jeff L. Kraus, San Jose; Hugh R. Sharkey, Redwood City; Michael J. Horzewski, San Jose, all of Calif.

[73] Assignee: Danforth BioMedical Incorporated, Menlo Park, Calif.

[21] Appl. No.: 784,841

[22] Filed: Nov. 6, 1991

Related U.S. Application Data

[63] Continuation-in-part of Ser. No. 615,721, Nov. 19, 1990, abandoned.

[51] Int. Cl.⁵ .................. A61M 37/00; A61M 29/00
[52] U.S. Cl. ............................... 604/95; 604/96; 606/194
[58] Field of Search ................... 604/95–103, 604/280, 164–170; 606/192–196; 128/656–658, 772, 207.14, 207.15

[56] References Cited

U.S. PATENT DOCUMENTS

| | | | |
|---|---|---|---|
| 3,703,899 | 11/1972 | Calinog . | |
| 3,978,863 | 9/1976 | Fettel et al. | 606/192 |
| 4,284,081 | 8/1981 | Kasper et al. | 604/97 |
| 4,362,150 | 12/1982 | Lombardi, Jr. et al. | 604/99 |
| 4,545,367 | 10/1985 | Tucci | 604/96 |
| 4,723,936 | 2/1988 | Buchbinder et al. | 604/95 |
| 4,813,934 | 3/1989 | Engelson et al. | 604/99 |
| 4,848,344 | 7/1989 | Sos et al. | 604/96 |
| 4,917,088 | 4/1990 | Crittenden | 606/194 |
| 4,917,666 | 4/1990 | Solar et al. | 604/95 |
| 4,931,036 | 6/1990 | Kanai et al. | 604/99 |
| 4,998,923 | 3/1991 | Samson et al. | 606/194 |
| 5,047,018 | 9/1991 | Gay et al. | 604/164 |
| 5,047,045 | 9/1991 | Arney et al. | 606/194 |
| 5,085,636 | 2/1992 | Burns | 604/99 |

FOREIGN PATENT DOCUMENTS

WO86/06285 11/1989 PCT Int'l Appl. .

*Primary Examiner*—C. Fred Rosenbaum
*Assistant Examiner*—Mark Bockelman

[57] ABSTRACT

A dilatation balloon catheter with a non-removable guidewire is disclosed in which the guidewire is joined to the catheter tube through a distortable element, preferably a twistable tube. The element provides a strong fluid-tight connection between the guidewire and catheter tube and yet permits the guidewire to be rotated relative to the catheter tube over a wide range of rotation, with little torsional stress on either the catheter tube, the balloon or any other element of the catheter construction. In preferred embodiments, the catheter construction further includes a column support tube inside the balloon, surrounding a segment of the guidewire toward its distal end, to prevent collapse of the balloon along its longitudinal axis as the balloon is advanced into a stenosis. In these embodiments, the distortable element is joined to the catheter tube through the column support tube which thus serves as an intermediate linkage.

48 Claims, 13 Drawing Sheets

FIGURE 5 C

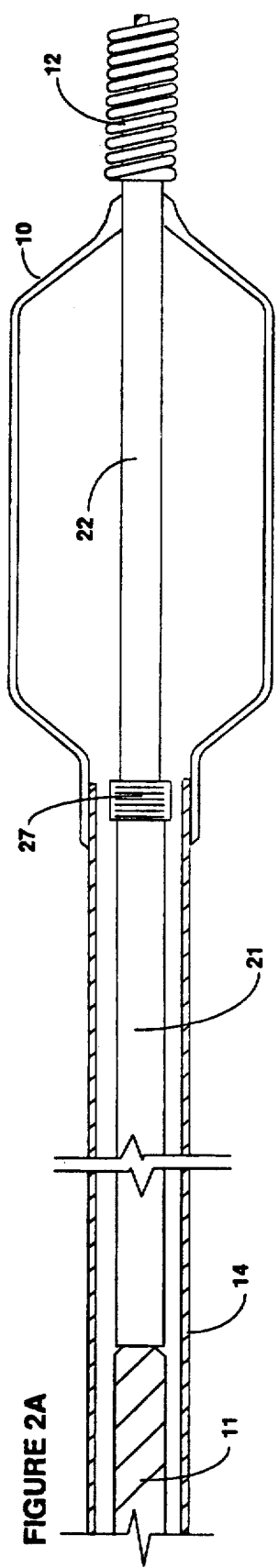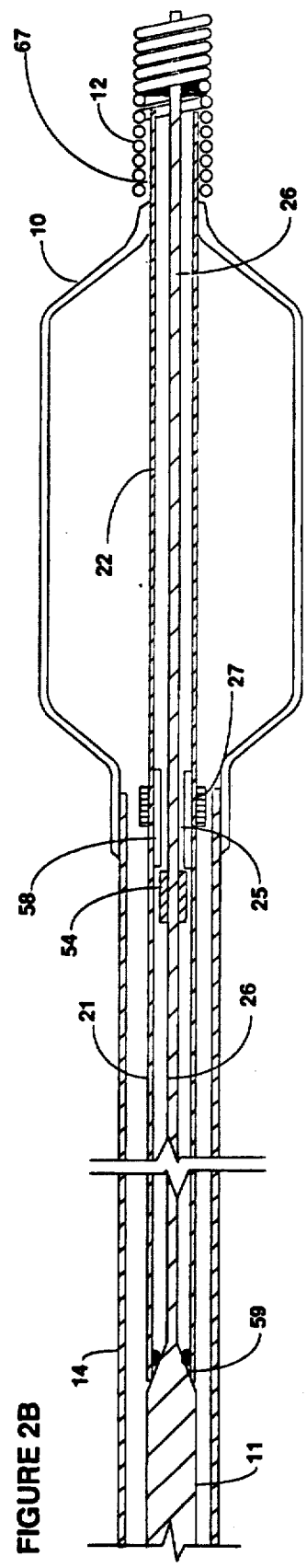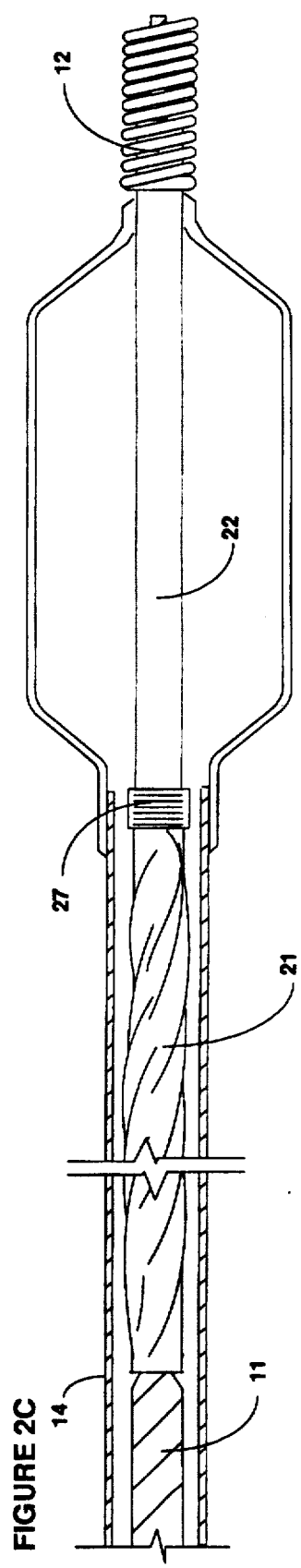

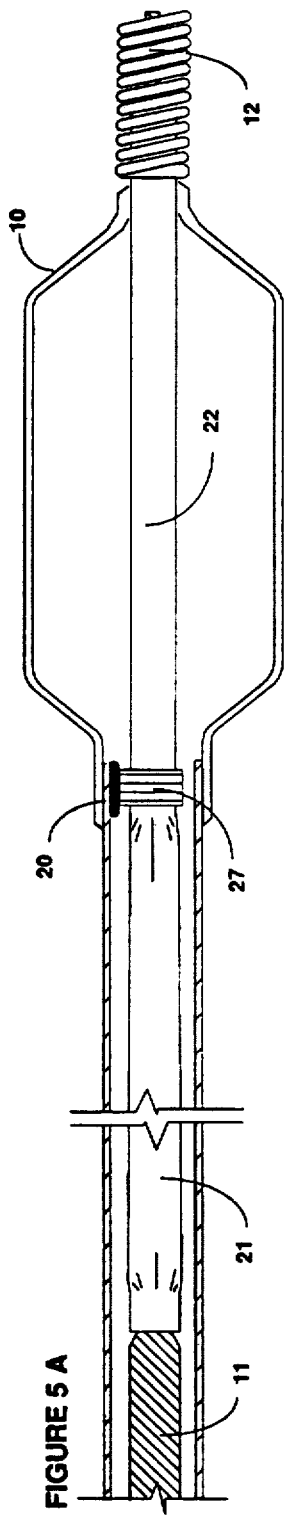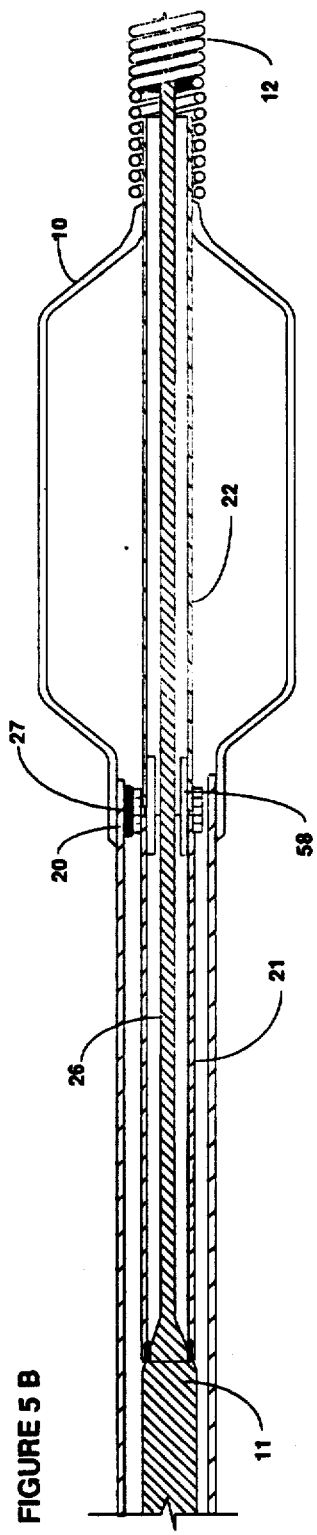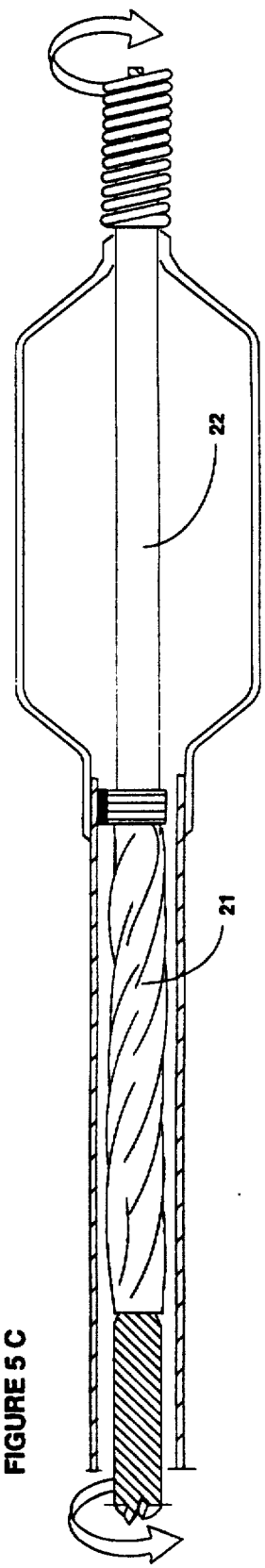

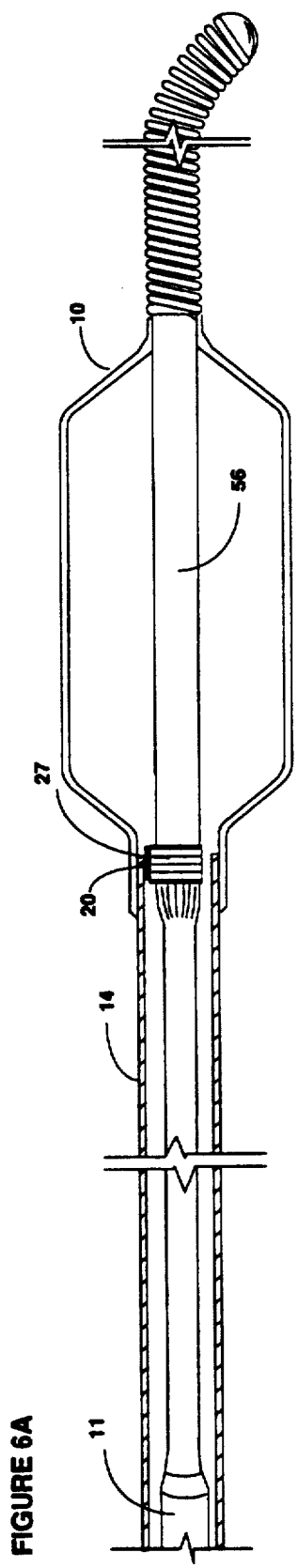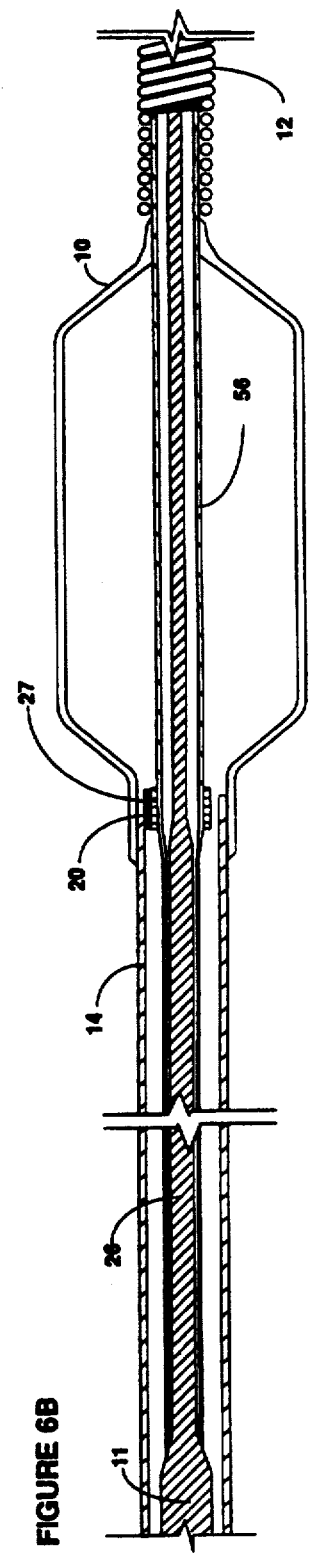
FIGURE 6A
FIGURE 6B

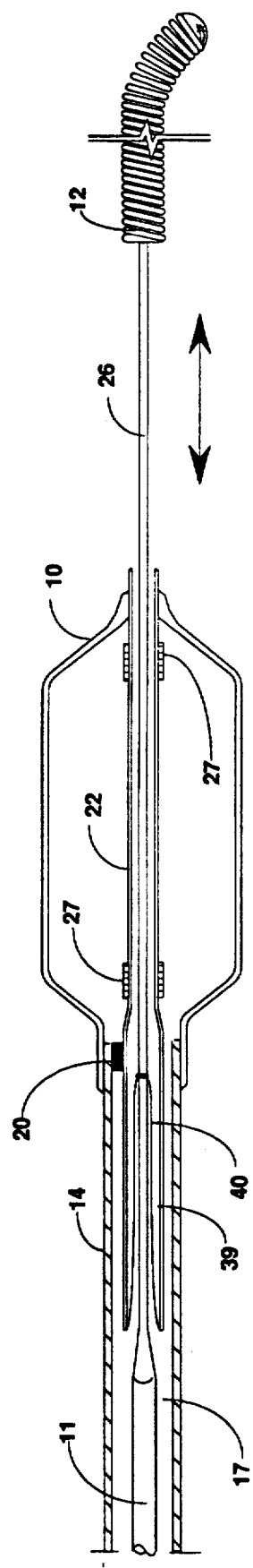
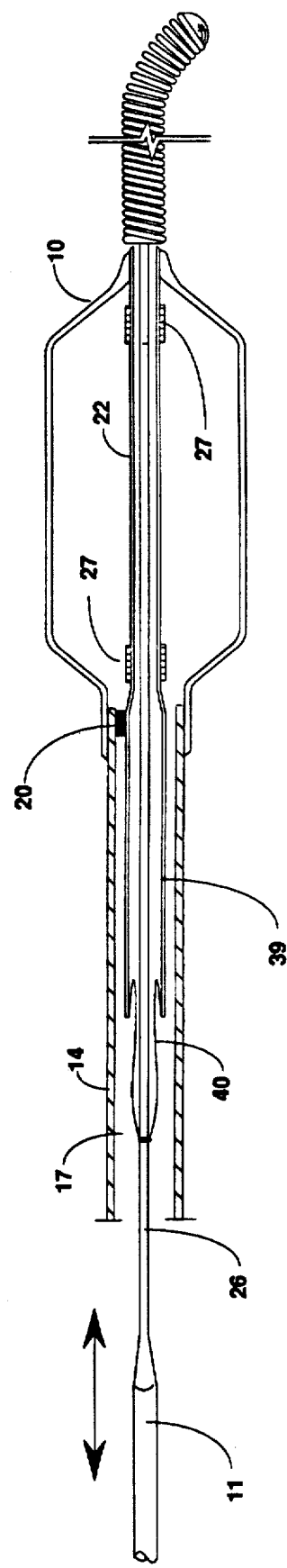
FIGURE 8 A
FIGURE 8 B

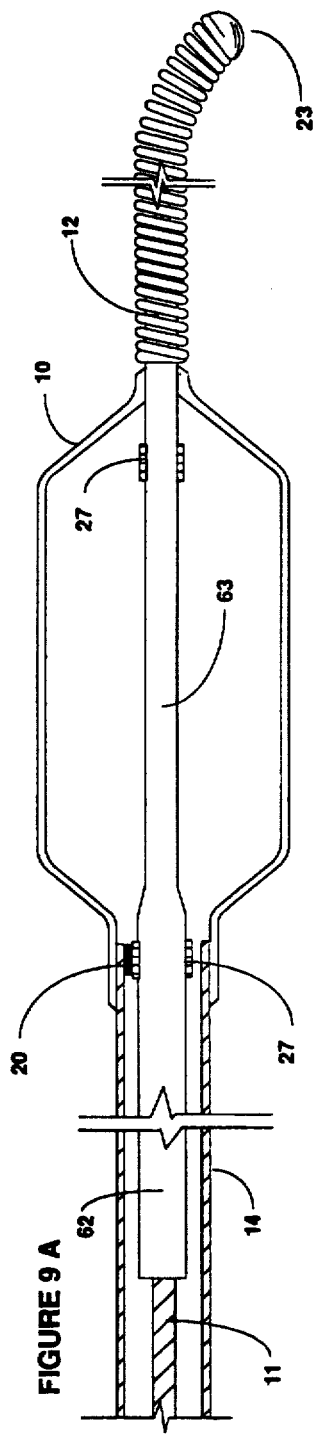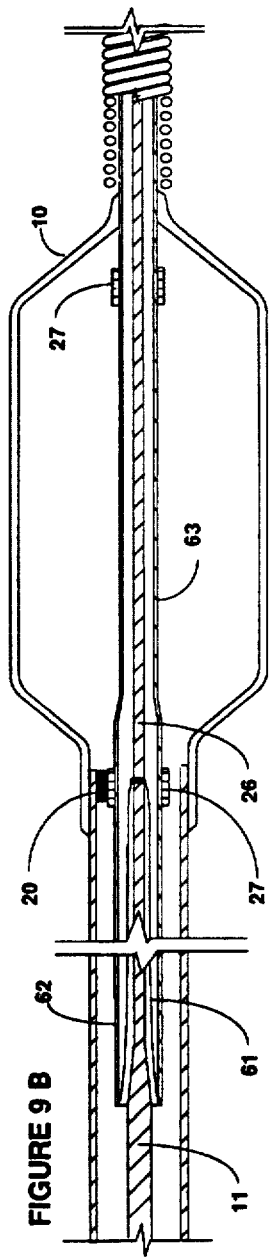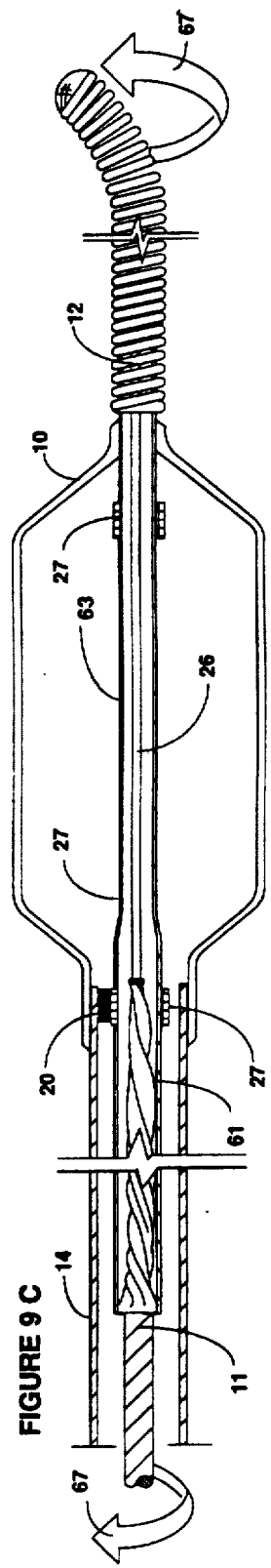

HIGHLY STEERABLE DILATATION BALLOON CATHETER SYSTEM

CROSS REFERENCE TO RELATED APPLICATION

This application is a continuation-in-part of copending application Ser. No. 07/615,721, filed Nov. 19, 1990 now abandoned.

This invention relates to catheters, and in particular to dilatation balloon catheters, including both intravascular dilatation balloon catheters which are percutaneously and intraoperatively installed and urologic dilatation balloon catheters.

BACKGROUND OF THE INVENTION

In 1977, Dr. Andreas Grüntzig first used a balloon-tipped flexible catheter to percutaneously dilate a region of stenosis within the coronary artery of a patient suffering from atherosclerotic heart disease. Since that time, the use of percutaneous transluminal coronary angioplasty has increased exponentially, and over the past eight to ten years, has become a routine procedure in many major medical centers throughout the world. With the advent of improved technology and operator skill, the indications for and use of this procedure have increased substantially. With such increased use, a need has developed for systems which have a low "crossing profile" (cross-sectional diameter of the balloon in the deflated state), low "shaft profile" (cross-sectional diameter of the catheter body), high "pushability" (resistance to collapse along the axial direction) and high "steerability" (directional control within the course of a body vessel). The reasons are as follows.

Lower profile systems offer several advantages over their larger profile counterparts. Systems with lower crossing profiles offer lowered resistance during advancement within the vasculature, and consequently offer greater ease of installation across the confines of intravascular lesions relative to comparable systems of larger crossing profile. A further advantage is that these systems can be used in critical lesions that cannot accommodate catheters of larger profile crossing profile. Systems with lower shaft profiles provoke less interruption to the surrounding flow of fluids (i.e., blood, blood substitutes, contrast medium and medications) following introduction within the vasculature, and are thus less prone to provoke ischemia, impair the delivery of medications and compromise the resolution of intraoperative angiography, relative to comparable systems of larger crossing profile.

Systems with greater pushability are easier to advance through regions of the vasculature that provoke resistance to catheter introduction relative to systems that provide inferior pushability. For purposes of this discussion, the term "pushability" will be used to denote the degree to which the catheter component of the system can be advanced into the vasculature without experiencing axial compression. Axial compression is the twisting, gathering or any other form of bending back of the balloon or shaft along the longitudinal axis of the system, which might occur in response to friction from the vasculature or, in the case of percutaneous transluminal coronary angioplasty, in response to friction from the guiding catheter which conducts the angioplasty catheter-guidewire system from the vascular access site to the origin of the coronary artery requiring treatment.

Systems with greater steerability are easier to direct through tortuous regions of the vasculature requiring treatment relative to those with less steerability, and thus offer a variety of features to balloon-mediated intravascular dilatation, including enhanced safety, facility and efficiency. Thus, the ease of positioning a catheter system for use varies directly with its "steerability" and "pushability," and inversely with the "crossing" and shaft profile of the system.

The shaft profile of a catheter-guidewire system varies with the number of channels contained within the catheter shaft. Other things being equal, multi-channel systems have larger profile shafts relative to single-channel systems. The pushability of a catheter system varies directly with the axial rigidity of the structural element (typically the guidewire mandrel or catheter body) that provides axial support to the system. Guidewire mandrels are constructed of stainless steel, which is less compliant than the polymeric materials commonly used in the construction of catheter bodies. For this reason, systems that rely upon the guidewire mandrel for column support (i.e., support of the balloon against axial compression) typically provide superior pushability relative to systems that rely upon the catheter body for this purpose.

The steerability of a catheter-guidewire system, in general, depends on the ease with which the guidewire can be rotated within a body vessel. This rotational mobility of the guidewire in turn is directly related to the ease with which the guidewire can be rotated relative to the catheter component. The reason is that the catheter component in most guidewire-directed catheter systems is substantially larger in external profile than the guidewire, and hence more difficult to rotate within a body vessel. The extent to which the catheter component must rotate in order to achieve rotation of the guidewire component will therefore affect the rotational mobility of the guidewire. Hence, those systems in which the guidewire component rotates independently relative to the catheter component offer superior steerability.

The original catheter conceived by Dr. Grüntzig is disclosed in Grüntzig, A., et al., U.S. Pat. No. 4,195,637, Apr. 1, 1980. Use of this device was abandoned in the early 1980's following the introduction of "over-the-wire" systems which offered both exchangeability and superior steerability. One such catheter is that disclosed by Simpson, J. B., et al., U.S. Pat. No. 4,323,071, Apr. 6, 1982. The term "exchangeability" denotes the ability of the guidewire and the catheter body to be separated while inside the vasculature for purposes of removing one or the other and replacing the removed component with a substitute component which differs in some respect, the exchange thereby taking place without the need to reestablish intraluminal access.

Although over-the-wire devices remain popular, experience has shown that these devices frequently cannot be advanced through the confines of critical lesions and thus cannot be used to treat such lesions. This limitation led to the development of "non-over-the-wire" systems, which have lower crossing profiles and frequently superior pushability relative to over-the-wire systems, and can thus be advanced within the confines of critical lesions that will not readily accommodate over-the-wire systems.

Non-over-the-wire systems include: (1) "semi-movable" catheter systems, (2) "fixed-wire" catheter systems, and (3) "balloon-on-a-wire" catheter systems. The guidewire components of these systems are permanently held inside the respective catheter tube and balloon components (i.e., the catheter components) of these systems. These systems differ among themselves however in the mobility of the guidewire components relative to the catheter components. An example is disclosed by Samson, W. J., et al, U.S. Pat. No. 4,616,653, Oct. 14, 1986. Fixed-wire catheters permit limited rotational and yet no coaxial mobility of the guidewire components relative to the catheter components. An example is disclosed by Samson, W. J., U.S. Pat. No. 4,582,181, Apr. 15, 1986. Balloon-on-a-wire systems permit no mobility of the guidewire components relative to the catheter components. An example of a balloon-on-a-wire device is disclosed by Crittenden, J. F., U.S. Pat. No. 4,917,088, Apr. 17, 1990.

Non-over-the-wire systems offer several structural and functional advantages relative to over-the-wire systems. Non-over-the-wire systems are generally easier to prepare and easier to advance across critical lesions. Such systems furthermore contain pre-installed guidewires and thus do not require preparation with guidewires. Still further, such systems can be advanced more easily through the confines of critical stenoses due to the lower crossing profiles of these systems and their superior pushability. In some respects, non-over-the-wire systems also offer safety advantages due to their lower shaft profiles: (1) the systems are less prone to provoke ischemia; (2) they are less prone to impair the delivery of medications; and (3) they permit the performance of intra-operative angiography with enhanced resolution.

These attributes have been achieved, however, at the expense of certain others. For example, none of these systems permit separation of the guidewire components from the catheter components. Hence, none of these systems are exchangeable and thus their use obligates sacrificing intraluminal access in the event of an exchange procedure. In the case of selected single-channel fixed-wire and balloon-on-a-wire systems, these attributes further have been achieved at the expense of steerability and structural integrity.

The advantages and disadvantages of selected fixed-wire and balloon-on-a-wire systems vis-à-vis over-the-wire systems relate, in part, to the practice of bonding the catheter component (and in particular the distal balloon component) to the guidewire component in the construction of these systems. Samson, W. J., U.S. Pat. No. 4,582,181, Apr. 15, 1986, discloses a single-channel fixed-wire system that contains one such bond at the distal catheter-guidewire interface. Crittenden, J. F., U.S. Pat. No. 4,917,088, Apr. 17, 1990, similarly discloses a single-channel balloon-on-a-wire system that contains such a bond at the distal catheter-guidewire interface. In these and similar systems, the bond between the balloon and guidewire serves several functions:

(1) It joins the distal aspect of the balloon to the guidewire;
(2) It prevents fluid and gas leakage from the distal aspect of the hydraulic channel and balloon; and
(3) It permits the guidewire to support the balloon against the possibility of axial collapse as the balloon is being advanced through a stenosis.

In short, these bonds enable the construction of airtight, hydraulically competent, guidewire-directed non-over-the-wire systems with single channels and guidewire-mediated column support. Stated differently, these bonds permit these devices to be constructed with lower shaft profiles and superior pushability relative to over-the-wire systems, which do not contain such bonds and rely upon the respective catheter bodies for column support. For these and other reasons, these bonds are fundamental to the structure and function of selected single-channel fixed-wire and balloon-on-a-wire devices.

Bonding the balloon to the guidewire, however, comprises the steerability of fixed-wire and balloon-on-a-wire systems. This bond tethers the guidewire to the catheter tube as well, and as a result the rotational resistance of both the catheter tube and the balloon is transmitted to the guidewire. This in turn limits the ease with which the guidewire can be rotated within a body vessel, thereby compromising the steerability of the entire composite system. For practical purposes, therefore, the ease with which the guidewire can be rotated relative to the catheter tube in fixed-wire devices such as that disclosed by Samson, W. J., U.S. Pat. No. 4,582,181, Apr. 15, 1986, is limited by the balloon's ability to accommodate torsion. Generally, these devices permit two or three complete (360°) turns of the guidewire in each direction relative to the catheter tube.

In addition to compromising steerability, the presence of a bond between the balloon and the guidewire compromises the structural integrity of single-channel fixed-wire and balloon-on-a-wire systems. In fixed-wire systems, the bond renders the device susceptible to over-wrapping of the balloon. When the guidewire in devices such as those disclosed by Samson, W. J., U.S. Pat. No. 4,582,181, Apr. 15, 1986, is given more than three complete turns in one direction relative to the catheter component, the balloon becomes tightly wrapped over the guidewire. Further rotation of the guidewire relative to the catheter component (and hence the balloon) generates increasing torsion within the balloon and guidewire. This raises the risk of causing tears in the balloon and fractures in the guidewire. To prevent such balloon wrapping and the occurrence of tears and fractures, torque limiters have been developed. An example is disclosed in U.S. Pat. No. 4,664,113 to Frisbie, J. S., et al., May 12, 1987.

The presence of the bond similarly compromises the structural integrity of balloon-on-a-wire systems. These systems typically do not provide any mobility of the guidewire component relative to the catheter component. Directional control of these systems is accomplished by rotating the entire system. During the treatment of critical lesions, the balloon components of these systems can become "hung up" within the confines of a body vessel, and will thus resist rotation. If the operator continues to apply rotational torque to the guidewire in an attempt to overcome this resistance and thereby restore directional control to the system, sufficient torsion may accumulate in the region of the bond to fracture the delicate distal segment of the guidewire or to tear the thin walls of the balloon.

From the foregoing, it is evident that there is a need for non-over-the-wire devices that have the crossing profile and pushability of a fixed-wire or balloon-on-a-wire device and yet afford greater guidewire rotational mobility and hence superior directional control and structural integrity than these systems presently offer, and that are simple in design and amenable to construction by mass production techniques. Such devices would enable one to perform an angioplasty within the confines of critically stenotic lesions with enhanced safety, facility, efficiency and finesse. These and other objects are addressed by the present invention.

SUMMARY OF THE INVENTION

In accordance with the present invention, a non-over-the-wire catheter system is provided in which the connecting structure between the guidewire and the catheter tube includes a distortable element which twists to accommodate the rotation of the guidewire within the catheter tube without interfering with the ability of the balloon to inflate or with the flow of fluids between the catheter lumen and the balloon. The distortable element comprises a length of flexible tubing, disposed over and coaxial to the guidewire component of the system, one end of which is secured to the guidewire component by a fluid-tight bond, while the other end is secured to the distal inner lumen of the balloon component, either directly or indirectly, by a fluid-tight bond. This distortable element constitutes a segment of the inner surface of the hydraulic channel of the system and functions to: (1) retain fluid under pressure, (2) permit limited rotational mobility of the guidewire component relative to the catheter component of the system, and (3) minimize the development of potentially damaging shear forces at the distal catheter-guidewire interface during guidewire rotation. The distortable element may be located anywhere along the length of the catheter, from the balloon interior to locations in the catheter lumen close to the catheter's proximal end without permitting loss of fluid and yet without interfering with the pressurization and depressurization of the balloon. The distortable element is thus comprised of liquid-permeable, and preferably both liquid- and gas-permeable, yet twistable material.

In preferred embodiments, the distortable element is combined with a non-distortable tubular element to form a continuous length of tubing, with the non-distortable tubular element connected to the catheter tube. The connection between the distortable element and the catheter tube is thus an indirect one, with the non-distortable tube serving as an intermediate linkage. The non-distortable tube is one which is resistant to twisting (rotational distortion) and to column collapse (axial distortion), and in preferred embodiments is secured inside the catheter in such a way as to provide column support for the balloon, i.e., support against collapse of the balloon along the balloon's longitudinal axis, as the balloon is being advanced through a stenosis. The distortable and non-distortable tubular elements can be constructed from a single length of tubing, treated differently along its length to render the tubing distortable at one end and non-distortable at the other end, or from a plurality of tubular elements distinct from each other in composition and distortability, joined end-to-end by means of fluid-tight and pressure tolerant seals. In these embodiments, the guidewire is coaxial to, and extends through the confines of, the distortable and non-distortable elements. This combination of distortable and non-distortable elements preserves the hydraulic integrity of the system, provides rotational mobility to the guidewire, provides guidewire-enhanced column support to the balloon component and minimizes the development of shear forces consequent with guidewire rotation.

Column support for the balloon can be provided in a variety of different ways in catheter systems that employ the present invention. For example, the non-distortable tubular element may extend through the length of the balloon element and be secured at one end to the distal aspect of the balloon and at the other to the distal end of the catheter tube proximal to the balloon. Bonded to the catheter in this manner, the non-distortable tubular element provides column support to the balloon by directly maintaining axial elongation of the balloon. In an alternative embodiment, the guidewire contains a stop which cooperates with a shoulder on the non-distortable element and thereby confers column support from the guidewire component to the distal aspect of the balloon, and thus axial elongation of the balloon. This embodiment provides superior pushability because column support is derived from the guidewire itself. The length of the non-distortable element in this embodiment is not critical to the column support, and the non-distortable element may therefore be reduced in length or eliminated entirely. The distortable element in this embodiment may be located either inside or outside the balloon.

By varying the composition, structure and length of the distortable element, particularly when the distortable element is twistable tubing, one can vary the extent to which the guidewire can be rotated inside the catheter tube, and thereby attain a high degree of guidewire rotational mobility and catheter steerability. The distortable element permits this to occur with minimal shear force on the other components of the catheter. This is achieved, furthermore, with a shaft, guidewire, hydraulic channel and crossing profile that are comparable in size to those of comparable single-channel fixed-wire and balloon-on-a-wire systems of the prior art.

In each of its various embodiments, therefore, the present invention permits one to construct air-tight, fluid-tight and pressure-tolerant catheter systems which have the advantageously narrow shaft profile of a single-channel non-over-the-wire system, the advantageously narrow crossing profile of a non-over-the-wire system, and the advantageously superior pushability of a non-over-the-wire system (which system relies upon the guidewire for coaxial support), and yet offer substantially enhanced rotational guidewire mobility, steerability, and structural integrity relative to air-tight systems of the prior art. Other features and advantages of the invention will be apparent from the description which follows.

BRIEF DESCRIPTION OF THE DRAWINGS

FIGS. 2A–2C illustrate a fixed-wire system similar to that of FIGS. 1A–1C. FIGS. 2A–2C are all side views of the distal portion of the system. In FIG. 2A, only the catheter shaft, balloon and guidewire mandrel are shown in cross section, whereas in FIG. 2B, all parts are shown in cross section. FIG. 2C shows the distortable element in the distorted state upon rotation of the guidewire within the catheter.

FIGS. 3A and 3C show only the catheter shaft, balloon and guidewire mandrel in cross section, and FIG. 3B shows all elements in cross section. FIG. 3C shows the distortable element in the distorted state.

FIGS. 5A-5C illustrate a fifth example of the invention. Again, only the distal portion is shown, with FIGS. 5A and 5C showing only the catheter shaft, balloon and guidewire mandrel in cross section, and FIG. 5B showing all elements in cross section. FIG. 5C shows the distortable element in the distorted state.

Figure 6C:
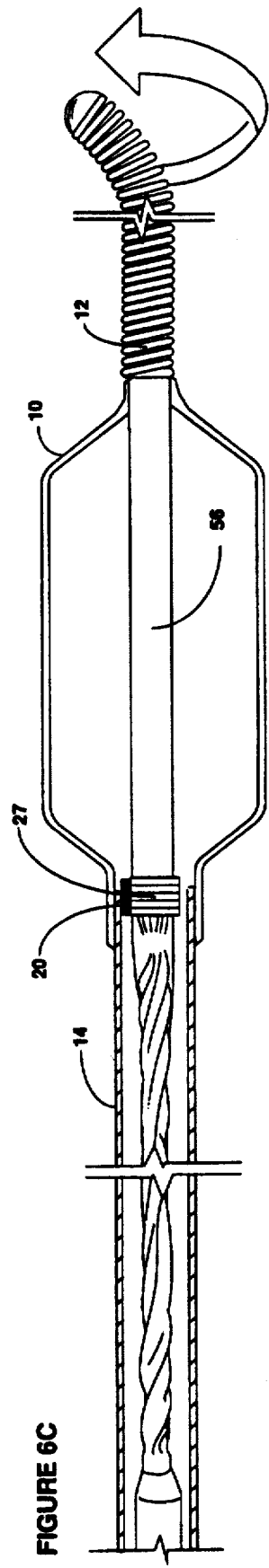

A sixth example is shown in FIGS. 6A-6C, with views corresponding to those of FIGS. 2A-2C, 3A-3C, and 5A-5C.

Figure 7:
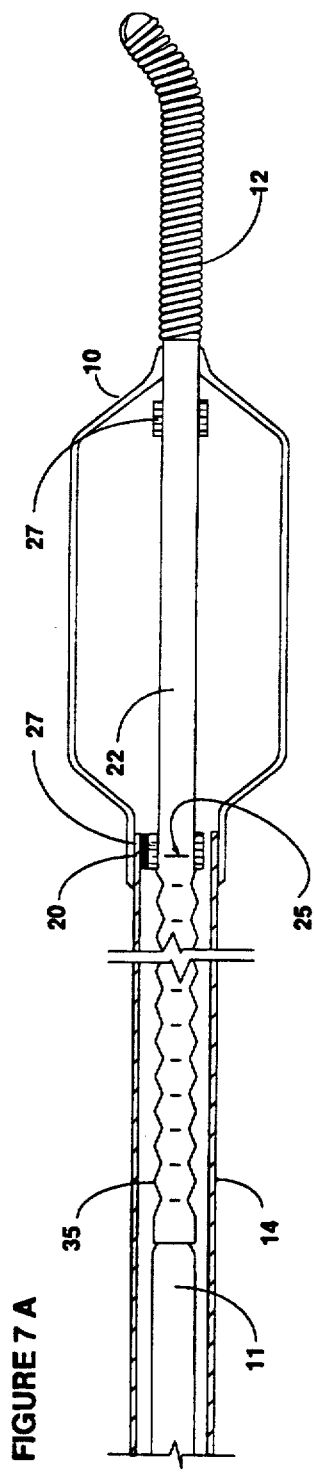
Figure 7:
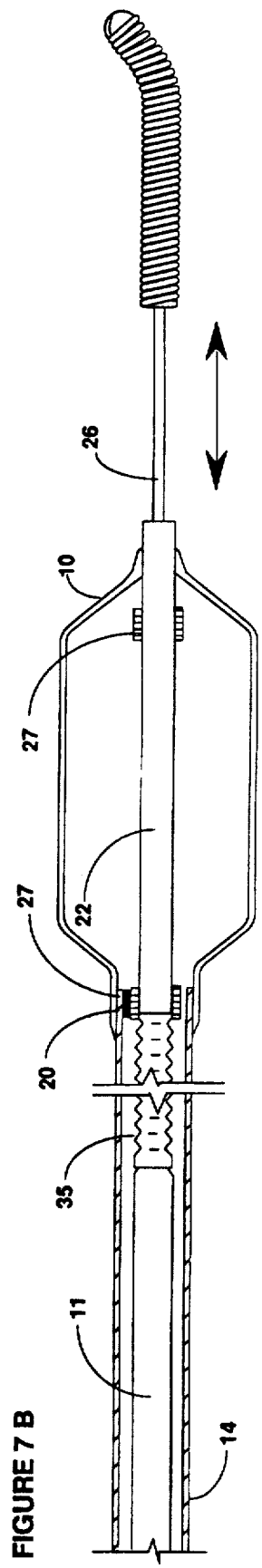

FIGS. 7A and 7B are side views of the distal portion of a seventh example of the invention, with the balloon and catheter shaft in cross section. The distortable element in this example has a bellows-type construction to accommodate axial elongation or compression in response to axial movement of the guidewire, in addition to the element's ability to twist to accommodate torsional forces. The system is thus a semi-movable system. FIG. 7A shows the appearance of the system with the guidewire fully retracted, and FIG. 7B shows the appearance of the system with the guidewire fully advanced or extended.

FIGS. 8A and 8B are side views of the distal portion of an eight example of the invention, which again has a semi-movable attribute. In these views, the catheter shaft, the balloon, the distortable element and the non-distortable tube are shown in cross section.

FIGS. 9A-9C are side views of the distal portion of a ninth example of the invention. FIG. 9A shows the catheter tube, balloon and guidewire in cross section; FIG. 9B shows all elements in cross section; and FIG. 9C shows the catheter tube, balloon, guidewire and non-distortable tube in cross section, with the distortable tube in a distorted state.

Figure 10:
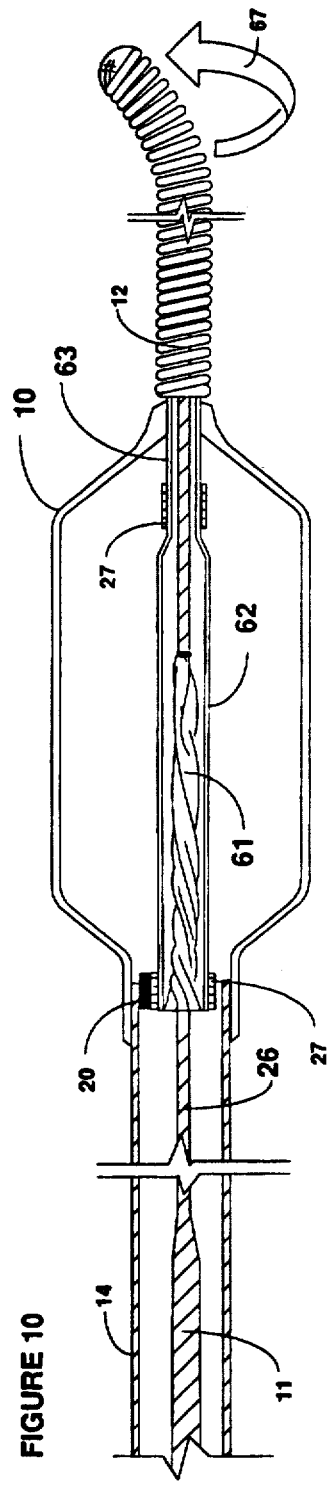

FIG. 10 is a side view of the distal portion of a tenth example of the invention, with all elements except the distortable element in cross section.

Figure 11:
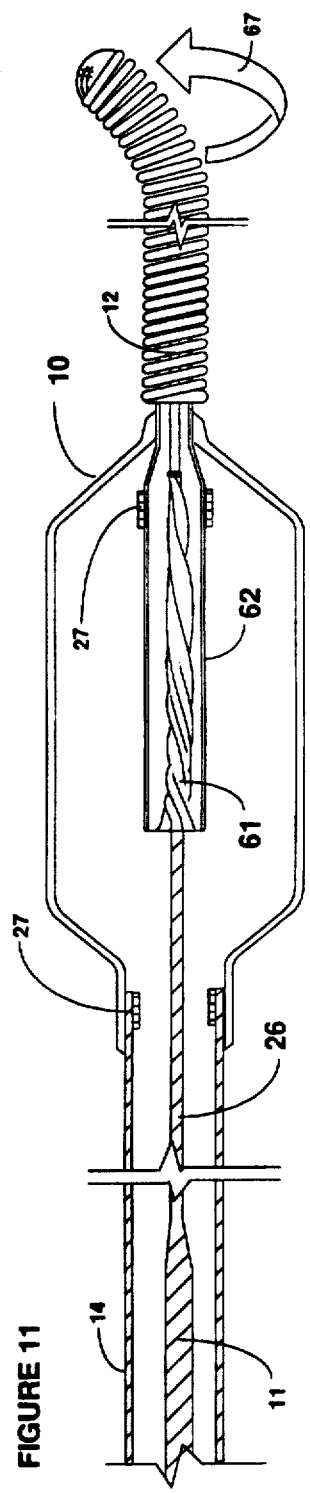

FIG. 11 is a side view of the distal portion of an eleventh example of the invention, with all elements except the distortable element in cross section.

Figure 12:
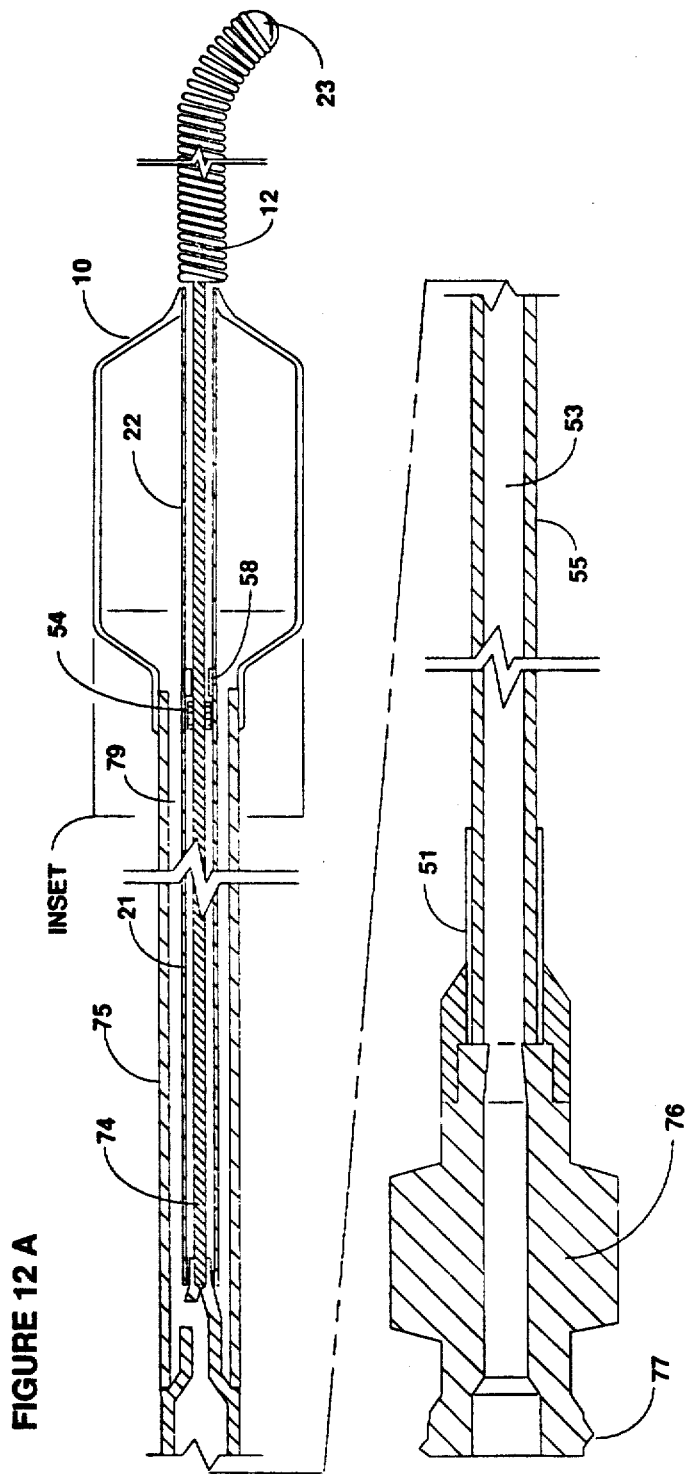
Figure 12:
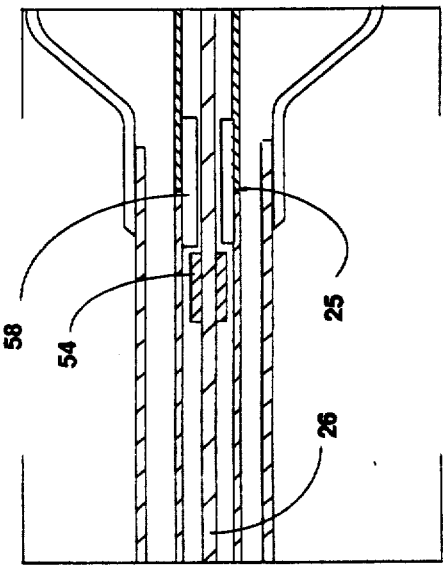

FIGS. 12A and 12B are side views of a twelfth example of the invention, in a balloon-on-a-wire system. FIG. 12A is a full side view of the system in full cross section, and FIG. 12B is an enlargement of the portion of FIG. 12A labeled "INSET."

DETAILED DESCRIPTION OF THE INVENTION AND PREFERRED EMBODIMENTS

Figure 1A:
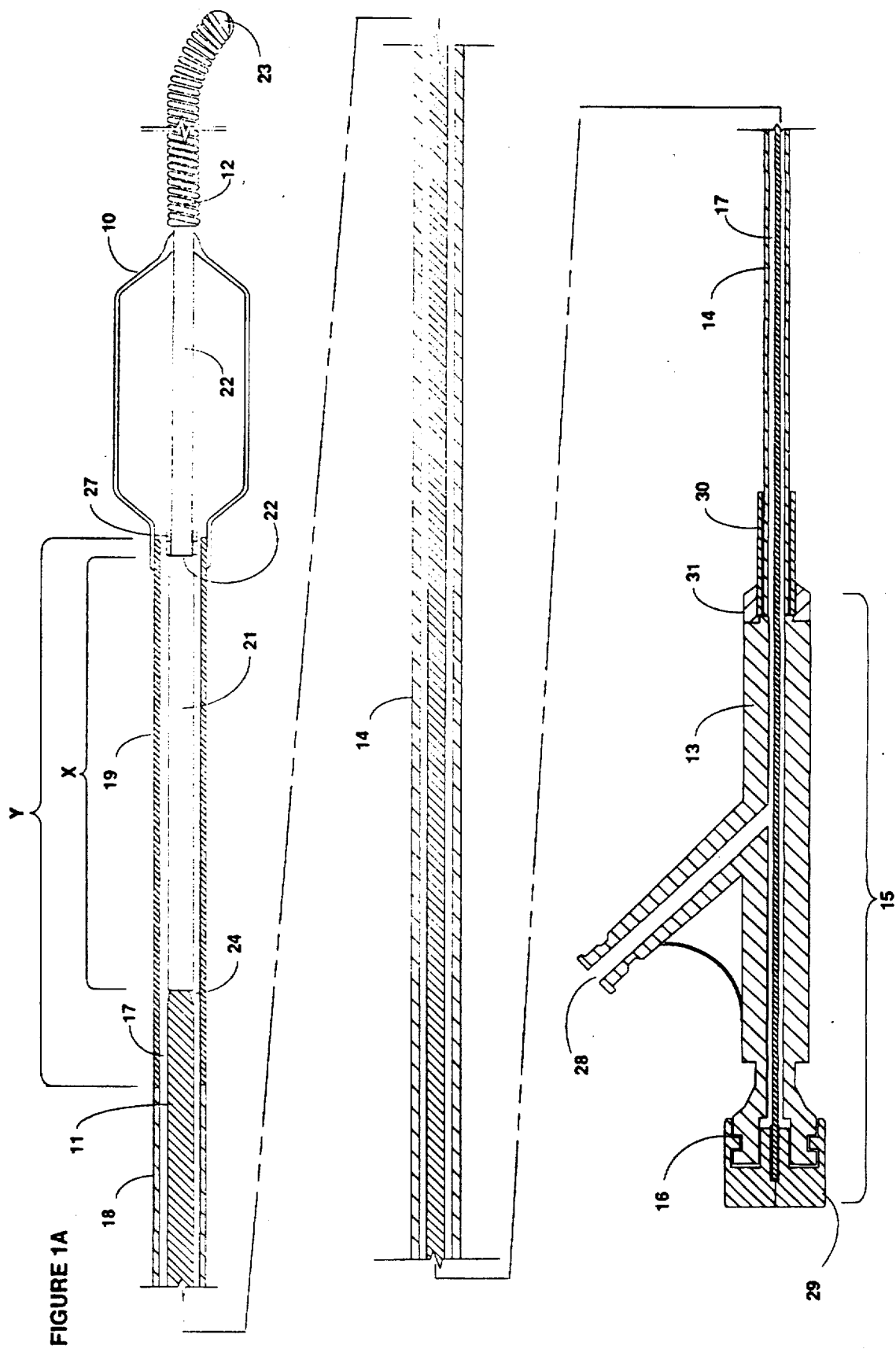
FIG. 1A is a side view of one example in which the invention may be incorporated in a fixed-wire catheter/guidewire system. The view is in cross section except for the distortable element and a non-distortable tubular element.
Figure 1B:
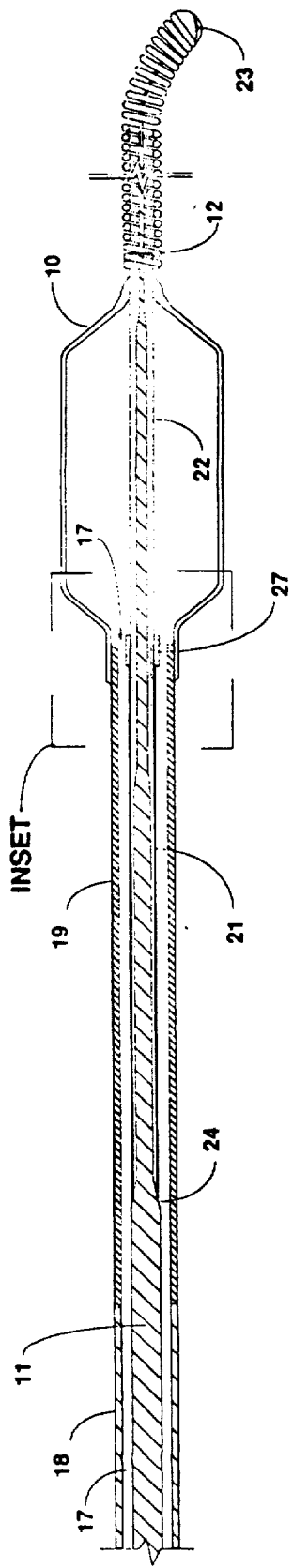
FIG. 1B is a full cross-section view of the distal end of the system of FIG. 1A.

FIG. 1 illustrates the application of the present invention to a particular fixed-wire catheter construction. This catheter (not shown to scale) includes a balloon 10, a guidewire with a tapered mandrel 11 (shown more clearly in FIG. 1B), an outer catheter shaft or tube 14, and a proximal adapter 15. The distal end of the guidewire passes through two tubular elements 21, 22 inside the outer catheter tube 14 and the balloon 10 and terminates in a tip coil 12 emerging from the catheter end.

The balloon component 10 is formed of conventional high strength polymeric material. Such material provides a balloon which is both tolerant to high pressure and thin-walled.

The outer catheter tube 14 is preferred embodiments of this invention is constructed in two or more butt-joined segments. The embodiment of FIG. 1A includes two such segments 18, 19 joined by a hydraulically competent bond. The distal end of the distal segment 19 is joined to the proximal end of the balloon 10. By selecting materials of differing flexibility for the different segments, one achieves a catheter of improved pushability (resistance to axial compression) and steerability (ease of advancement within the tortuous confines of the vasculature) relative to catheters with outer catheter tubes of uniform rigidity. The proximal segment 18 of the embodiment of FIG. 1A, for example, is more rigid than the distal segment 19. For catheters of the standard length of 130-140 cm, the distal segment 19 has a length Y which measures approximately 20-30 cm.

Of the two inner tubular elements 21, 22, the more distal 22 of the two is relatively rigid and extends the full length of the balloon 10, while the more proximal element 21 is relatively flexible. The distal element 22 is the element providing column support for the balloon, while the proximal element 21, whose proximal end is bonded to the surface of the guidewire 11, is the distortable element which twists to accommodate the turning of the guidewire relative to the outer catheter tube 14. In this embodiment, the distortable element 21 extends from the proximal end of the balloon to the most proximal taper 24 of the guidewire mandrel 11. For a catheter of the standard 120-140 cm length, this distance X measures 20-30 cm. This distance can be shortened or lengthened, however, to accommodate the requirements of the system. For similar reasons, the length of the distortable element 21 can be lengthened or shortened relative to the low profile (small diameter) segment of the guidewire mandrel 11. Detailed descriptions of various forms of the distortable and non-distortable elements appear below. A preferred material for the distortable element 21 is PEBAX, a urethane-nylon composition manufactured by Atochem, Inc., of Glen Rock, N.J., while a preferred material for the column support tube 22 is polyimide.

In this embodiment, the distal end of the distortable element 21 is bonded to the proximal end of the column support element 22 at a joint 25, while the proximal end of the distortable element 21 is bonded to guidewire mandrel 11 at the first taper 24. The distal end of the column support element 22 is joined to the distal luminal surface of the balloon 10 at a joint 26. These joints and inner tubular elements, together with the exposed portion of the guidewire 11 proximal to the most proximal taper 24, form the inner radial boundary of a closed annular hydraulic channel 17, which is the space lying between these surfaces and the inner surface of the outer catheter shaft 14. The hydraulic channel 17 extends the length of the device and is in fluid communication with the interior of the balloon 10. The channel serves to convey hydraulic fluid and transmit hydraulic pressure along the length of the device.

The column support element 22 is resistant both to twisting and to collapse along its longitudinal axis. At its proximal end, the column support element 22 abuts a support chip or flange 54 (visible in FIG. 1C) affixed to the guidewire mandrel in a manner that permits rotational mobility of the column support element 22 and yet resists coaxial mobility of the element relative to the guidewire mandrel. This configuration enables the guidewire to impart column support to the balloon component of the system without compromising the rotational mobility of the guidewire component relative to the catheter component, and thus the steerability of the composite system. In contrast to the column support element 22, the distortable element 21 is twistable and thereby provides rotational mobility of the guidewire mandrel 11 relative to the outer catheter tube 14. The flexibility of the distortable element 21 permits it to wrap around its long axis in response to the application of torsional force. Since the distortable element 21 is not relied upon for providing column strength to the balloon and since it is supported by the underlying guidewire 11 during balloon inflation, the distortable element 21 can be constructed with particularly thin walls.

The guidewire 11 terminates at its distal end in a radiopaque tip coil 12 and shaping ribbon (not shown). The proximal end of the tip coil 12 and shaping ribbon are attached to the guidewire 11 at a location immediately distal to the balloon 10. The proximal end of the guidewire coils extend of the distal end of the catheter to provide a smooth transition between the catheter and guidewire, and yet one with sufficient clearance to permit rotational mobility of the guidewire relative to the catheter tube 14. The distal end of the tip coil 12 is secured to the distal end of the shaping ribbon at a tip joint 23. The guidewire mandrel 11 and tip coil 12 are rotationally mobile relative to the balloon 10 and the column support element 22.

A marker band 27, which is radiopaque or of otherwise detectable material, is secured to the proximal end of the column support element 22. Thus positioned at opposite ends of the balloon, the marker band 27 and tip coil 12 permit one to precisely identify the location of the balloon 10 during tracking of the catheter by fluoroscopic or otherwise appropriate methods.

The proximal adapter 15, shown in reduced scale at the bottom of FIG. 1A, consists of a rotational element 29 and a stationary element 13 that are joined by means of a fluid-tight, high pressure tolerant interface 16 that limits intercomponent rotational mobility in either direction to a preset number of complete turns. An example of one such rotation limiter is disclosed in co-pending U.S. patent application Ser. No. 07/709,572, filed Jun. 3, 1991. Typical devices of this construction will accommodate approximately six to thirty complete turns in either direction. The rotational element 29 is bonded to the proximal aspect of the guidewire 11. The operator rotates the rotational element 29 to rotate the guidewire and thereby steer the composite device within the confines of the vasculature.

The stationary element 13 contains at least one sideport 28. The open end of this sideport is designed to mate with male Luer Lock components (not shown). The sideport 28 provides access to the hydraulic channel 17, and the balloon 10 is inflated by infusion of fluid into the sideport 28. A strain relief element 30 spans the interface between the proximal adapter and the outer surface of the outer catheter tube 18. The strain relief element is attached to the catheter tube and the stationary element 13 by means of a cap 31.

Figure 1C:
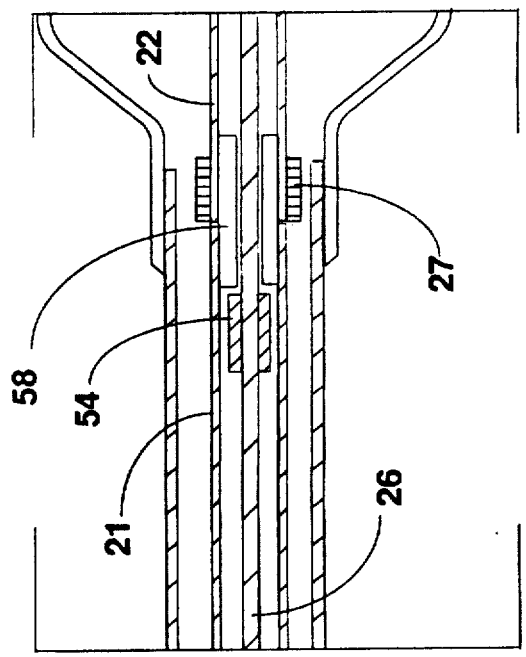
FIG. 1C is an enlarged view of the portion of FIG. 1A labeled "INSET."

FIG. 1B is a view of the distal aspect of the device shown in FIG. 1A, in full cross section. This figure illustrates the tapered configuration of the guidewire mandrel 11, as well as the structural relationship of the guidewire to the remaining components of the device. FIG. 1C is an enlargement of the "INSET" portion of FIG. 1B, indicating the spatial relationships of the column support element 22, the distortable element 21, a shoulder 58 extending around the inner surfaces of the both the column support element 22 and the distortable element 21 at their juncture, the marker band 27, and the guidewire flange 54.

To achieve column support, the balloon must be prevented from longitudinal collapse in the reverse axial direction (to the left in the view shown in the drawings) as the structure is advanced through a vasculature in the forward axial direction (to the right). Since both the balloon 10 and the distortable element 21 are sufficiently flexible to be vulnerable to this type of axial compression, the structure utilizes the guidewire 11 to maintain axial support of the distortable tubular element 21. This support is in turn transmitted to the balloon 10 by the column support element 22.

Axial support of the distortable tubular element 21 is provided by the flange 54 which encircles the guidewire mandrel 11. The flange 54 abuts the shoulder 58 on the inner surfaces of the distortable and column support elements, thereby serving as a stop which prevents the tubular distortable element 21 from collapsing longitudinally toward the left. The flange 54 is capable of rotation relative to the shoulder 58, so that the guidewire remains free to rotate relative to the outer catheter tube, but the flange is incapable of axial movement past the shoulder. Column support is thus achieved without any kind of proximal bond, and with improved fluid communication between the annular hydraulic channel 17 of the catheter and the interior of the balloon 10.

FIGS. 2A, 2B and 2C are detailed profile views of the distal aspect of a device like that of FIGS. 1A-1C, differing only in the taper configuration of the guidewire mandrel 11. All other parts of the system are identical to those of FIGS. 1A-1C. The distortable element 21, the column support element 22 and the marker band 27 are shown in full view rather than cross section in FIGS. 2A and 2C. FIG. 2B is a full cross section view illustrating the spatial relationships of the various components of this portion of the device, and particularly the relationship of the column support element 21 relative to the guidewire flange 54. FIG. 2C illustrates the change in configuration which the distortable element 21 undergoes upon rotation of guidewire 11 relative to the catheter shaft 14. This change is a twisting of the distortable element about its longitudinal axis and the wrapping of the distortable element around the guidewire, in response to the torsional force caused by rotation of the guidewire. The torsional force required to twist the element in this manner is minimal.

By utilization of the features illustrated in FIGS. 1A-2C, one can construct an air-tight, fluid-tight and pressure-tolerant low-profile fixed-wire dilatation balloon delivery system with advantages over single-channel fixed-wire systems of the prior art that contain adhesive bonds at the distal catheter-guidewire interface. These advantages include:

(a) superior structural integrity, i.e., diminished propensity to sustain over-rotation of the balloon component, torsionally-mediated tears within the balloon walls and fratures within the guidewire mandrel, and (b) superior guidewire rotational mobility and hence superior steerability.

These advantages are achieved while retaining pushability, shaft profile, crossing profile and hydraulic performance commensurate with the single-channel fixed-wire prior art systems. When comparing systems incorporating these features with over-the-wire systems of the prior art, further advantages are obtained. These include superior pushability, superior shaft profile and superior crossing profile. Furthermore, systems incorporating these features are simple to construct and amenable to manufacture with conventional mass production techniques.

Figure 3A:
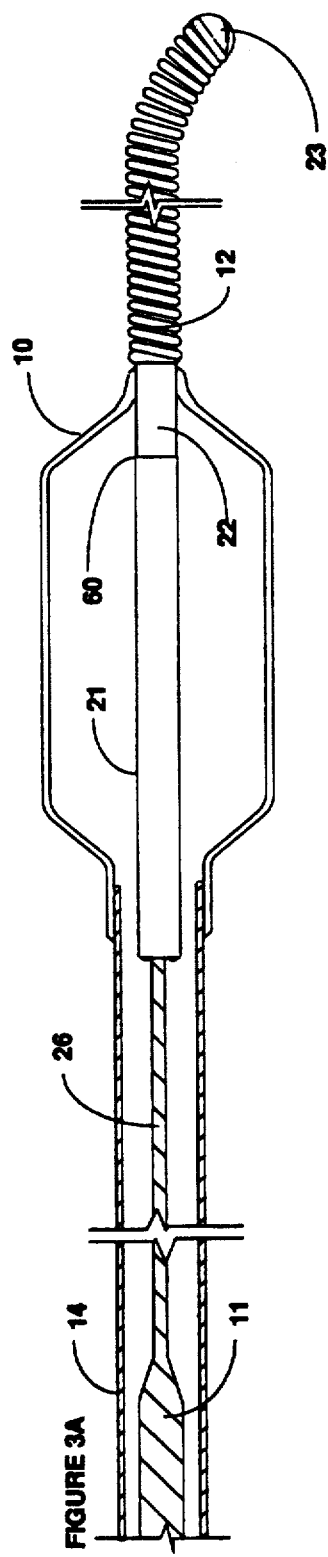
FIGS. 3A–3C illustrate side view of the distal portion of a third example of the invention.
Figure 3B:
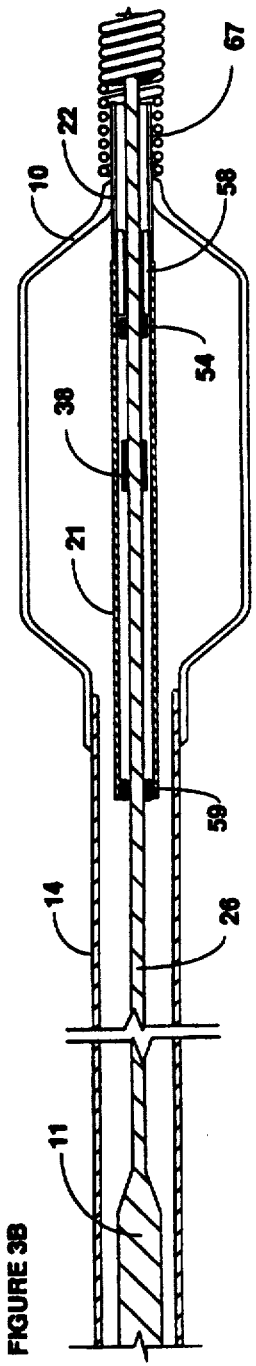
Figure 3C:
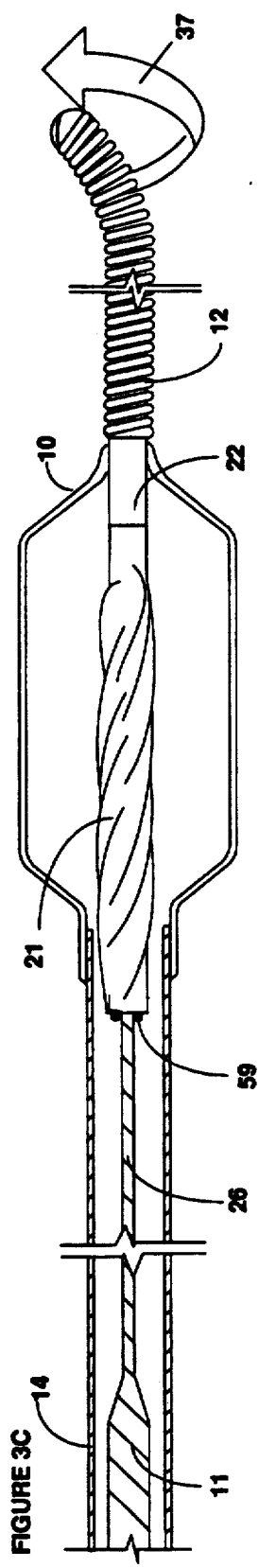

FIGS. 3A, 3B and 3C are similar profile views of the distal aspect of another dilatation balloon catheter-guidewire device within the scope of this invention, slightly different from the devices of FIGS. 1A-2C. In FIGS. 3A and 3C, the distortable element 21, the column support element 22 and the marker band 27 are shown in full view rather than in cross section, with FIG. 3C illustrating the change in configuration which the distortable element 21 undergoes upon rotation of guidewire 11 relative to the catheter shaft 14 in the direction indicated by the arrow 37. FIG. 2B is a full cross section illustrating the spatial relationships of the various components. The device of FIGS. 3A, 3B and 3C differs from that of FIGS. 2A, 2B and 2C by virtue of: (1) the length of the column support element 22, (2) the spatial relationship of the guidewire flange 54 to the marker band 38, and (3) the spatial relationship of the marker band 38 to the distortable element 21. In the device of FIGS. 3A, 3B and 3C, the marker band 38 is disposed inside the distortable element 21 and is attached directly to the guidewire 11.

Figure 4:
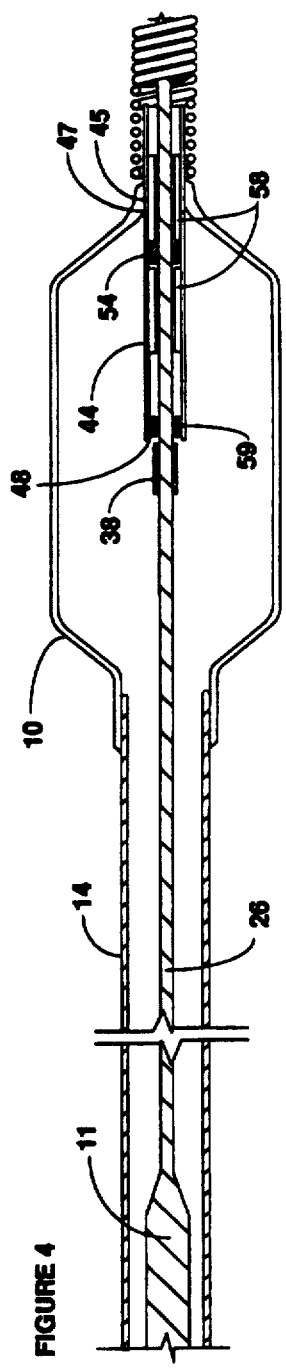
FIG. 4 illustrates a fourth example, with all elements in cross section.

In the structure shown in FIG. 4, the column support element 45 and the distortable tubular element 44 have been shortened. Both the distal end 47 and the proximal end 48 of the distortable element 44 lie inside the balloon. In this embodiment, axial support of the balloon component is provided by shoulders 58 which are bonded to the inner luminal surfaces of the distortable and column support elements 44, 45, and which straddle the guidewire flange 54 in a manner that permits rotational mobility of the guidewire mandrel 11 relative to the tubular elements. A steerable fixed-wire catheter-guidewire system constructed in this manner offers a potentially lower crossing profile and potentially superior flexibility (and hence trackability) within the region of the balloon 10 relative to the systems described above.

A further dilatation balloon catheter-guidewire device within the scope of this invention is shown in FIGS. 5A, 5B and 5C. The views correspond to those of FIGS. 2A-2C and FIGS. 3A-3C. The differences here are: (1) the length of the column support element 22 which here extends the full length of the confines of the balloon 10, (2) the presence of a bond 20 joining the proximal end of the column support element 22 to the luminal surface of the outer catheter tube 14 (which bond extends around only a portion of the circumference of the tube, thereby leaving room for fluid communication), and (3) the location of the marker band 27. Unlike the embodiments illustrated in FIGS. 3A-3C and 4, the balloon component of this device is supported axially by the outer catheter tubing 14 and not the guidewire mandrel 11.

By using the arrangement of elements shown in FIGS. 5A-5C, one can construct highly steerable low-profile fixed-wire devices which afford catheter shaft-mediated pushability. This arrangement can also be used in the construction of semi-movable devices. As indicated above, semi-movable devices provide variable rotational and limited coaxial guidewire mobility. The use of an elastomeric material in the construction of the distortable element 21 of this embodiment provides the guidewire with limited mobility in both rotational and axial directions relative to the outer catheter tube 14. A suitable elastomeric material for this application is a urethane-nylon composition such as PEBAX, manufactured by Atochem, Inc., of Glen Rock, New Jersey. Like the distortable elements of the preceding figures, this elastomeric tubular segment 21 is interposed between the guidewire 11 and the column support element 22.

The differences between typical semi-movable systems (not shown in the drawings hereto) and typical fixed-wire systems lie in the configuration of the proximal adapter (which is not shown in FIGS. 5A-5C) and in the number of marker bands. Unlike the fixed-wire system described previously, a semi-movable system may for example contain a marker band at the distal aspect of the balloon in addition to the marker band at the proximal aspect. The use of a pair of marker bands facilitates monitoring of the balloon location by fluoroscopy or other appropriate means as the catheter is being advanced through the vasculature.

FIGS. 6A, 6B and 6C are profile views of the distal aspect of yet another embodiment of a catheter-guidewire system of the present invention. The views here as well correspond to those of FIGS. 2A-2C and FIGS. 3A-3C. The differences in this embodiment lie in the construction of the distortable and column support elements. Unlike the embodiments described above, the distortable and column support elements of this embodiment are constructed from a single length of tubing 56. In the case of this embodiment, the wall of one portion of the tubing 56 (the left half in the view shown in the drawings) has been thinned relative to the other to provide this segment with enhanced flexibility.

FIGS. 7A and 7B are two profile view of the distal aspect of yet another embodiment of a catheter-guidewire system of the present invention. Like the embodiments described above, this embodiment also provides limited rotational and axial mobility of the guidewire relative to the catheter, but differs by providing axial mobility with enhanced ease. FIG. 7A shows the profile appearance of the distal aspect of the device with the guidewire fully retracted, while FIG. 7B shows the profile appearance of the device with the guidewire advanced relative to the catheter. While the device is similar in other respects to those of FIGS. 5A-5C and 6A-6C, the difference lies in the design and construction of the distortable element 35. This element, which is preferably constructed of PET (polyethylene terephthalate), contains a series of corrugations which permit expansion and contraction of the element along its longitudinal axis, as well as rotation. These corrugations permit this expansion and contraction to occur with minimal force and with no risk of damage or fluid obstruction. In addition, upon the exertion of a torsional force, the element wraps easily around the guidewire.

Any tubular element or tubular configuration that is fluid-tight, capable of withstanding elevated pressures without breakage, and that both twists rotationally and extends and contracts longitudinally, can be used in place of the corrugated construction of the element 35 shown in FIGS. 7A and 7B in the construction of a semi-movable device with a lower shaft profile than prior art devices. Consistent with the differences noted above between semi-movable and fixed-wire constructions, the semi-movable device of FIGS. 7A and 7B has a special proximal adapter (not shown) which permits the axial mobility of the guidewire, and two marker bands, one 27 at the proximal aspect of the balloon and the other 28 at the distal aspect.

FIGS. 8A and 8B are cross section profile views of another embodiment of a catheter-guidewire system of the present invention, this one, like that of FIGS. 7A and 7B, being another semi-movable device. FIG. 7A illustrates the appearance of the device with the guidewire in the fully retracted condition, while FIG. 7B illustrates the appearance of the device with the guidewire fully extended. The distortable element in this embodiment consists of a relatively rigid component 39 and a relatively flexible component 40, both tubular in form. The flexible component 40 affords both axial and rotational mobility to the guidewire mandrel 11. The flexible component 40 folds backward over itself as the guidewire is being advanced through the catheter, permitting mobility of the guidewire between the retracted position shown in FIG. 8A and the extended position shown in FIG. 8B. The column support element 22 is narrower but otherwise similar to that of FIGS. 7A and 7B. Note that in each of these configurations the rigid component 39 of the distortable element maintains a constant configuration and orientation, as do all other system components at the distal end of the catheter, and the hydraulic channel 17 remains fully sealed.

Variations on the embodiment of FIGS. 8A and 8B are shown in FIGS. 9A, 9B, 9C and 10. In these variations, the distortable element again consists of two components 61, 62, one of which 61 is both rotationally twistable and longitudinally stretchable, and the other 62 is relatively rigid. The twistable and stretchable component 61 may for example be constructed of an elastomeric material. The column support element 63 is analogous to that of the previous Figures.

In the embodiment of FIGS. 9A-9C, FIG. 9A illustrates the distal aspect of the device with only the balloon 10, the catheter shaft 14 and the guidewire mandrel 11 in cross section. FIG. 9B shows the device in full cross section with the twistable and stretchable element 61 in a relaxed (neither twisted nor stretched) configuration, while FIG. 9C shows the device with only the balloon 10, catheter shaft 14, guidewire mandrel 11 and rigid elements 62, 63 in cross section, to show the twistable and stretchable element 61 in a twisted condition caused by rotation of the guidewire in the direction indicated by the arrows 67.

The embodiment of FIG. 10 is similar to that of FIGS. 9A-9C (in the same view as that of FIG. 9C) except for the length of the column support element 63, which is shortened sufficiently to place the distortable element 61 entirely within the confines of the balloon.

The embodiment shown in FIG. 11 is analogous to that of FIGS. 9A-9C and 10, except that both components 61, 62 of the distortable element have been shortened as well, and there is no bond between any of the inner tubular elements and the catheter shaft 14, such as the bond 20 shown in FIGS. 9A-9C and 10. In addition, the column support element has been eliminated entirely, and its function has been transferred to the rigid component 62 of the distortable element. The twistable component 61 of the distortable element twists in response to the rotational force caused by rotation of the guidewire in the direction indicated by the arrow 67 but, unlike the corresponding components of the embodiments of FIGS. 9A-9C and 10, this component does not stretch axially. Column support for the balloon is thus achieved by the axial tension on the twistable component 61 as the guidewire 11 and the catheter shaft 14 are urged forward (to the right according to the view shown in the drawing). With the distortable element residing entirely inside the balloon, it is expected that the crossing profile of the device illustrated in this Figure will be lower than the crossing profiles of the devices illustrated in FIGS. 9A-9C and 10, where either all or part of the distortable element resides outside (at the proximal end of) the inflatable portion of the balloon.

FIG. 12A illustrates a balloon-on-a-wire device which incorporates the present invention. FIG. 12B is an enlargement of the region at the proximal end of the balloon, labeled "INSET" in FIG. 12A, to illustrate in detail the structural relationships of the various components in this region.

The balloon-on-a-wire device of FIGS. 12A and 12B includes a guidewire component which consists of a length of stainless steel hypodermic needle tubing 55, such as that sold under the trademark HYPOTUBE by Popper & Sons, Inc., New Hyde Park, N.Y., U.S.A., which is continuous with a guidewire mandrel 74, which in turn extends through the confines of the balloon 10 and terminates within the confines of the tip coil 12. Surrounding the mandrel 74 is a flange 54. The tip coil 12 is secured to the mandrel 74 by means of a solder joint 20, a ball tip 23 and a shaping ribbon (not shown) inside the tip coil.

The catheter component includes a catheter tube 75, a balloon 10 secured to the distal end of the catheter tube 75, a column support tube 22, and a distortable element 21. The lumen 79 of the catheter tube 75 communicates with the interior of the balloon 10 and with the channel 53 of the stainless steel tubing. The column support tube 22 and the distortable element 21 are bonded together by means of a butt joint, and together constitute the inner tubular member of the device. The distal end of the column support tube 22 is secured to the distal end of the balloon 10 whereas the proximal end of the distortable element 21 is secured to the guidewire mandrel 74 at some point proximal to the balloon 10 along the length of the mandrel 74. The column support tube 22 is rotationally disposed over the mandrel 74. Column support for the balloon 10 is provided by a flange 54 on the guidewire that engages a shoulder 58 which extends around the inside surface of the column support tube 22.

At the proximal end of the device, the stainless steel tubing 55 is secured to a proximal adapter 76. This adapter is designed to receive a Luer-Lock component by an appropriate fitting 77, and contains a hydraulic channel 60 which is continuous with the stainless steel tubing channel 53, and thus the catheter tube lumen 79 and the interior of the balloon 10. Direction control of the device is accomplished by rotating the entire device. In the event that the balloon becomes caught within the confines of a body vessel such that the catheter component fails to move when the guidewire is manipulated, it is anticipated that the distortable element 22 will diminish the development of shear forces within the distal regions of the system. The distortable element thereby provides the system with superior structural integrity relative to systems that contain adhesive bonds at the distal catheter-guidewire interface. Inflation and deflation of the balloon 10 are accomplished by infusing and withdrawing fluid through the channel 53.

Each of these embodiments and others within the scope of the invention offer the advantages of superior directional control over non-over-the-wire structures of the prior art, without loss of the benefits of the low crossing profiles, the option to prepare the device in dry condition, and the pushability, all of which are characteristic of such structures. The versatility and scope of the concept permit its application to semi-movable structures as well as fixed-wire and balloon-on-a-wire structures, and the invention as a whole enables one to perform angioplasty procedures with less effort and with greater efficiency, safety and finesse relative to the prior art. The embodiments are furthermore simple to construct and thus amenable to mass production.

The foregoing descriptions are offered primarily for purposes of illustration. It will be readily apparent to those skilled in the art that the construction of the system, the materials, the type, arrangement and location of components, and other parameters of the system may be further modified or substituted in various ways without departing from the spirit and scope of the invention.

What is claimed is:

1. A catheter-guidewire assembly comprising:
   an outer tubular member terminating in proximal and distal ends, said outer tubular member defining a lumen and having a longitudinal axis defining an axial direction;
   balloon means mounted to said distal end of said outer tubular member, said balloon means having proximal and distal ends and an interior which is in fluid communication with said lumen of said outer tubular member;
   a guidewire disposed within said outer tubular member in a manner permitting rotation of said guidewire relative to said outer tubular member in a rotational direction about said longitudinal axis, said guidewire having a terminus extending through and protruding beyond said distal end of said balloon means; and
   an inner tubular member disposed coaxial to and encircling said guidewire and bonded both to said distal end of said balloon means and to said guidewire, thereby retaining fluid under pressure, said inner tubular member comprising, at least in part, a rotationally distortable connecting means permitting axial rotation of the guidewire relative to the balloon means about said longitudinal axis.

2. A catheter-guidewire assembly in accordance with claim 1 in which said rotationally distortable connecting means is a length of tubing.

3. A catheter-guidewire assembly in accordance with claim 1 in which said rotationally distortable connecting means is a length of tubing that is distortable both in said axial and rotational directions.

4. A catheter-guidewire assembly in accordance with claim 1 in which said rotationally distortable connecting means is a length of tubing that is liquid-impermeable.

5. A catheter-guidewire assembly in accordance with claim 1 in which said rotationally distortable connecting means is a length of tubing that is both liquid-impermeable and gas-impermeable.

6. A catheter-guidewire assembly in accordance with claim 1 in which said inner tubular member consists entirely of said rotationally distortable connecting means.

7. A catheter-guidewire assembly in accordance with claim 1 in which said inner member is comprised of said rotationally distortable connecting means and a length of non-axially-collapsible tubing.

8. A catheter-guidewire assembly in accordance with claim 7 in which said rotationally distortable connecting means is adjoined to said distal end of said balloon means through said non-axially collapsible tubing.

9. A catheter-guidewire assembly in accordance with claim 8 in which said non-axially collapsible tubing is secured to said outer tubular member in a manner retarding rotation of said non-axially collapsible tubing relative to said outer tubular member, and said rotationally distortable connecting means is adjoined to said outer tubular member through said non-axially collapsible tubing.

10. A catheter-guidewire assembly in accordance with claim 9 in which said length of non-axially collapsible tubing extends at least through the length of said balloon means and is bonded to said outer tubular member in a manner which permits fluid communication between said lumen and said balloon means.

11. A catheter-guidewire assembly in accordance with claim 1 further comprising column support means for maintaining elongation of said balloon means in said axial direction.

12. A catheter-guidewire assembly in accordance with claim 11 in which said column support means permits fluid communication between said lumen and said balloon.

13. A catheter-guidewire assembly in accordance with claim 11 in which said column support means permits axial rotation of said guidewire relative to said balloon means.

14. A catheter-guidewire assembly in accordance with claim 11 in which said column support means is comprised of a flange attached to said guidewire, said flange engaging a length of column support tubing within said balloon means, said column support tubing being non-axially-collapsible and having a distal end bonded to said distal end of said balloon means.

15. A catheter-guidewire assembly in accordance with claim 11 in which said column support means is comprised of a length of column support tubing extending through said balloon means, said column support tubing being non-axially-collapsible, and said balloon means having proximal and distal ends each bonded to said length of column support tubing.

16. A catheter guidewire assembly in accordance with claim 15 which permits longitudinal advancement, retraction and axial rotation of said guidewire relative to said outer tubular member.

17. A catheter guidewire assembly in accordance with claim 1 which permits longitudinal advancement and retraction of said guidewire relative to said outer tubular member.

18. A catheter-guidewire assembly in accordance with claim 1 in which said outer tubular element is a multi-component element which includes first and second lengths of tubing, said first length being proximal to said second length and relatively rigid with respect thereto.

19. A catheter-guidewire assembly in accordance with claim 1 in which a portion of said guidewire is disposed inside said inner tubular member and said portion of said guidewire is of a reduced diameter relative to the remainder of said guidewire.

20. A catheter-guidewire assembly in accordance with claim 1 that contains at least one radiopaque marker band within said balloon means interior or at said proximal end of said balloon means.

21. A catheter-guidewire assembly comprising:

an outer tubular member having proximal and distal ends, said outer tubular member defining a lumen and having a longitudinal axis defining an axial direction;

balloon means having proximal and distal ends with an opening at said distal end, said proximal end of said balloon means bonded to said distal end of said outer tubular member;

an inner tubular member extending through said balloon means, said inner tubular member bonded at one end to said balloon means opening and at the other end to said outer tubular member at a location between said proximal and said distal ends of said outer tubular member in a manner permitting fluid communication between said balloon and said outer tubular member, said inner tubular member being sufficiently non-collapsible in said axial direction to prevent axial collapse of said balloon;

a guidewire disposed within said outer tubular member and said inner tubular member and protruding through said opening in said balloon means; and a length of rotationally distortable tubing bonded at one end to said guidewire and at the other end to said inner tubular member to permit rotation of said guidewire relative to said inner tubular member while retaining fluid under pressure.

22. A catheter-guidewire assembly in accordance with claim 21 in which said inner tubular member and said length of rotational tubing each have proximal and distal ends and said distal end of said length of rotationally distortable tubing is bonded to said proximal end of said inner tubular member while said proximal end of said length of rotationally distortable tubing is bonded to said guidewire.

23. A catheter-guidewire assembly in accordance with claim 22 in which said inner tubular member is coextensive with said balloon means, whereby said distal end of said rotationally distortable tubing is at the same axial location as said proximal end of said balloon means.

24. A catheter-guidewire assembly comprising:

an outer tubular member terminating in proximal and distal ends, said outer tubular member defining a first lumen and having a longitudinal axis defining an axial direction;

balloon means mounted to said distal end of said outer tubular member, said balloon means having proximal and distal ends and an interior which is in fluid communication with said first lumen of said outer tubular member;

a guidewire comprising at least a length of steel tubing defining a second lumen and terminating in proximal and distal ends, and a length of wire extending distally from said distal end of said steel tubing, said distal end of said steel tubing being joined in fluid-tight manner to said proximal end of said outer tubular member in a manner that permits fluid communication between said second lumen and said first lumen, said length of wire disposed within said outer tubular member in a manner permitting rotation of said guidewire in a rotational direction about said longitudinal axis, said guidewire having a terminus extending through and protruding beyond said distal end of said balloon means; and an inner tubular member disposed coaxially relative to said outer tubular member and encircling said guidewire, said inner tubular member connecting said distal end of said balloon means to said guidewire, thereby retaining fluid under pressure, said inner tubular member comprising, at least in part, rotationally distortable connecting means permitting axial rotation of the guidewire relative to the balloon means about said longitudinal axis.

25. A catheter-guidewire assembly in accordance with claim 24 in which said rotationally distortable connecting means is a length of tubing.

26. A catheter-guidewire assembly in accordance with claim 24 in which said rotationally distortable connecting means is a length of tubing that is liquid-impermeable.

27. A catheter-guidewire assembly in accordance with claim 24 in which said rotationally distortable connecting means is a length of tubing that is both liquid-impermeable and gas-impermeable.

28. A catheter-guidewire system in accordance with claim 24 in which said inner tubular member consists entirely of said rotationally distortable connecting means.

29. A catheter-guidewire assembly in accordance with claim 24 in which said inner tubular member is comprised of said rotationally distortable connecting means and a length of non-axially-collapsible tubing.

30. A catheter-guidewire system in accordance with claim 24 in which said rotationally distortable connecting means is adjoined to the distal end of said balloon means through said non-axially-collapsible tubing.

31. A catheter-guidewire assembly in accordance with claim 30 in which said inner tubular member is secured to said outer tubular member in a manner prohibiting rotation of said inner tubular member relative to said outer tubular member and said rotationally distortable connecting means is adjoined to said outer tubular member through said inner tubular member.

32. A catheter-guidewire assembly in accordance with claim 31 in which said inner tubular member extends at least through the length of said balloon means and is bonded to said outer tubular member in a manner permitting fluid communication between said first lumen and said balloon means interior.

33. A catheter-guidewire assembly in accordance with claim 24 further comprising column support means for maintaining elongation of said balloon means in said axial direction.

34. A catheter-guidewire assembly in accordance with claim 33 in which said column support means permits fluid communication between said first lumen and said balloon means.

35. A catheter-guidewire assembly in accordance with claim 33 in which said column support means permits axial rotation of the said guidewire relative to said balloon means.

36. A catheter-guidewire assembly in accordance with claim 33 in which said column support means is comprised of a flange encircling said guidewire, said flange engaging a length of column support tubing within said balloon means, said column support tubing being non-axially collapsible and having a distal end bonded to said distal end of said balloon means.

37. A catheter guidewire assembly in accordance with claim 33 in which said column support means is comprised of a length of column support tubing extending through said balloon means, said column support tubing being non-axially-collapsible, and said balloon means having proximal and distal ends each bonded to said length of column support tubing.

38. A catheter-guidewire assembly in accordance with claim 24 in which a portion of said guidewire is disposed inside said inner tubular member and said portion of said guidewire is of a reduced diameter relative to the remainder of said guidewire.

39. A catheter-guidewire assembly in accordance with claim 24 that contains at least one radiopaque marker band within said balloon means interior or at said proximal end of said balloon means.

40. A catheter-guidewire assembly comprising:
an outer tubular member having proximal and distal ends, said outer tubular member defining a first lumen and having a longitudinal axis defining an axial direction;
balloon means having proximal and distal ends with an opening at said distal end, said proximal end of said balloon means bonded to said distal end of said outer tubular member;
an inner tubular member extending through said balloon means, said inner tubular member bonded at one end to said balloon opening and at the other end to said outer tubular member at a location between said proximal and said distal ends of said outer tubular member in a manner permitting fluid communication between said balloon and said outer tubular member, said inner tubular member being sufficiently non-collapsible in said axial direction to prevent axial collapse of said balloon;
a guidewire comprising at least a length of steel tubing defining a second lumen and proximally terminating in proximal and distal ends, and a length of wire extending distally from said distal end of said steel tubing, the distal end of said steel tubing being joined in fluid-tight manner to said proximal end of said outer tubular member in a manner that permits fluid communication between said second lumen and said first lumen, said length of wire disposed within said outer tubular member and said inner tubular member in a manner permitting rotation of said guidewire in a rotational direction about said longitudinal axis, said guidewire having a terminus extending through and protruding beyond said opening in said balloon means; and
a length of rotationally distortable tubing bonded at one end to said guidewire and at the other end to said inner tubular member to permit rotation of said guidewire relative to said inner tubular member while retaining fluid under pressure.

41. A catheter-guidewire assembly in accordance with claim 40 in which said inner tubular member and said length of rotationally distortable tubing each have proximal and distal ends, and said distal end of said length of rotationally distortable tubing is bonded to said proximal end of said inner tubular member while said proximal end of said length of rotationally distortable tubing is bonded to said guidewire.

42. A catheter-guidewire assembly in accordance with claim 40 in which said inner tubular member is coextensive with said balloon means, and whereby said distal end of said rotationally distortable tubing is at the same axial location as said proximal end of said balloon means.

43. A catheter-guidewire assembly comprising:
an outer tubular member having proximal and distal ends, said outer tubular member defining a lumen and having a longitudinal axis defining an axial direction;
balloon means having proximal and distal ends with an opening at said distal end, said proximal end of said balloon means bonded to said distal end of said outer tubular member;
a guidewire disposed within said outer tubular member, said guidewire having a flange mounted thereto, and said guidewire protruding through said opening in said balloon means;
an inner tubular member extending through said balloon means and encircling said guidewire, said inner tubular member having proximal and distal ends, said inner tubular member bonded at the distal end thereof to said balloon means opening and, at the proximal end thereof, abutting said flange, said inner tubular member being sufficiently non-collapsible in said axial direction to prevent axial collapse of said balloon; and
a length of rotationally distortable tubing bonded at one end to said guidewire and at the other end to said inner tubular member to permit rotation of said guidewire relative to said inner tubular member while retaining fluid under pressure.

44. A catheter-guidewire assembly in accordance with claim 43 in which said distortable connecting means is a length of tubing that is distortable in a rotational direction.

45. A catheter-guidewire assembly in accordance with claim 43 in which said distortable connecting means is a length of tubing that is liquid-impermeable.

46. A catheter-guidewire assembly in accordance with claim 43 in which said distortable connecting means is a length of tubing that is both liquid-impermeable and gas-impermeable.

47. A catheter guidewire assembly in accordance with claim 43 which permits longitudinal advancement and retraction of said guidewire relative to said outer tubular member.

48. A catheter-guidewire assembly in accordance with claim 43 in which said outer tubular element is a multi-component element which includes first and second lengths of tubing, said first length being proximal to said second length and relatively rigid with respect thereto.

* * * * *